(12) United States Patent
Tiollier et al.

(10) Patent No.: US 7,528,240 B2
(45) Date of Patent: May 5, 2009

(54) METHOD FOR PRODUCING HUMAN ANTI-THYMOCYTE IMMUNOGLOBULINS

(75) Inventors: Jérôme Tiollier, Marseilles (FR); Laurent Sorlin, Vaugneray (FR)

(73) Assignee: Sangstat Medical Corporation, Cambridge, MA (US)

( * ) Notice: Subject to any disclaimer, the term of this patent is extended or adjusted under 35 U.S.C. 154(b) by 341 days.

(21) Appl. No.: 10/381,859

(22) PCT Filed: Sep. 25, 2001

(86) PCT No.: PCT/FR01/02972

§ 371 (c)(1),
(2), (4) Date: Mar. 28, 2003

(87) PCT Pub. No.: WO02/26830

PCT Pub. Date: Apr. 4, 2002

(65) Prior Publication Data

US 2004/0023340 A1 Feb. 5, 2004

(30) Foreign Application Priority Data

Sep. 28, 2000 (FR) .................................. 00 12384

(51) Int. Cl.
*C07K 1/18* (2006.01)
(52) U.S. Cl. ...................... 530/417; 530/413
(58) Field of Classification Search ........................ None
See application file for complete search history.

(56) References Cited

U.S. PATENT DOCUMENTS

| | | | |
|---|---|---|---|
| 4,364,935 A | 12/1982 | Kung et al. | |
| 4,464,935 A | 8/1984 | McHugh | |
| 4,541,953 A * | 9/1985 | Thimel-Baumer | 530/389.6 |
| 5,304,637 A * | 4/1994 | Dorssers et al. | 530/351 |
| 5,578,480 A * | 11/1996 | Khandke | 435/232 |

FOREIGN PATENT DOCUMENTS

WO    WO 9947166 A1 *   9/1999

OTHER PUBLICATIONS

Verbanac et.al. Production of stable rabbit-mouse Heterohybridomas: . . . membrane antigen. Hybridoma, 1993; 12: 285-295.*
Thomas et.al. T cell-specific activity in rabbit anti-human thymocyte globulin. Ann. Surg., 1983; 198: 131.*
Azavedo et. al. Toxicity of staphylococcal toxic shock syndrome toxin 1 in rabbits. Infection and Immunity, 1984; 46: 314-317.*
Harlow et.al. Antibodies A Laboratory Manual. 1988, Cold Spring Harbor Laboratory, pp. 289, 292, 293 and 301.*
Harlow et al., Antibodies: A Laboratory Manual, Cold Spring Harbor Press, 1988, pp. 93, 94, 283-318 and 261-270.*
Thomas et al., Ann Surg. Sep. 1983;198(3):370-6.*
McKenzie et al., Med J Aust. Feb. 1, 1969;1(5):203-7.*
Tewari et al., Arch Virol. 1993;132(1-2):101-20.*
Chang et al., Vet Parasitol. Jul. 31, 1998;78(2):137-45.*
Rebellato et al., Transplantation. Mar. 15, 1994;57(5):685-94.*
Janeway et al., Immunobiology, 3rd Ed., Garland Science, pp. 6:1-6:9, (1997).*
Greco et al., Blood. Nov. 1983;62(5):1047-54.*
Raefsky et al., Blood, Sep. 1986;68(3):712-9.*
Janeway et al., Immunobiology, 3rd Ed., Garland Science, pp. 1:6-1:10.*
Beaufigeau, M., et al., "Seven-year experience with rabbit antithymocyte globulin after cardiac transplantation at the Montreal Heart Institute," *Transplant. Proc.* 29(7A):10S-12S (Nov. 1997).
Guttmann, R.D., et al., "Renal transplantation in the inbred rat. 3. A study of heterologous anti-thymocyte sera," *J. Exp. Med.* 126:1099-1127 (1967).
Préville, X., et al., "A quantitative flow cytometry assay for the preclinical testing and pharmacological monitoring of rabbit antilymphocyte globulins (rATG)," *J. Immunol. Meth.* 245(1-2):45-54 (Nov. 2000).
Rolland, J.M., "Anti-lymphocyte serum: a review of its immunological effects and therapeutic value," *Pathology* 4(2):85-122 (Apr. 1972).
Skopińska-Różewska, E, et al., "Search for the best schedule for production of nontoxic anti-thymocyte globulin," *Mater. Med. Pol.* 13(3):187-194 (Jul.-Sep. 1981).
Verschoor, E.J., et al., "Vaccination against feline immunodeficiency virus using fixed infected cells," *Vet. Immunol. Immunopathol.* 46(1-2):139-149 (May 1995).

* cited by examiner

*Primary Examiner*—Michail A Belyavskyi
*Assistant Examiner*—Zachary Skelding
(74) *Attorney, Agent, or Firm*—King & Spalding LLP

(57) ABSTRACT

Methods for producing improved anti-human thymocyte immunoglobulins from specific-pathogen-free animals are provided, without the need for an adsorption step on human tissues and the consequent drawbacks of such a step.

11 Claims, No Drawings

METHOD FOR PRODUCING HUMAN ANTI-THYMOCYTE IMMUNOGLOBULINS

FIELD OF THE INVENTION

The present invention relates to a method for producing anti-human thymocyte immunoglobulins.

BACKGROUND OF THE INVENTION

Anti-human thymocyte antibodies or immunoglobulins (Igs) are known to be selective immunosuppressants. They act on the immune response by decreasing, by depletion, according to various mechanisms, the quantity of circulating lymphocytes of the blood and of the various lymphoid tissues, and probably by blocking or modulating their receptors. Their use is indicated in the context of organ transplants, for the prevention and treatment of transplant rejection, and also for the treatment of acute graft versus host reaction. These immunoglobulins have also been proposed in the treatment of medullary aplasia.

Preparations of this type of immunoglobulin were initially obtained by injection of lymphatic cells into animals, rabbits or horses for example, and then by extraction of the anti-thymocyte immunoglobulins from the immune serum. However, the level of purity of these preparations was insufficient to render these immunoglobulins usable, in particular in therapy (R. D Guttman, 1967, J. Exp. Med., 126:1099-1127). Antihuman erythrocyte or anti-basal membrane immunoglobulins were in particular produced by the animal during the immunization. Several hypotheses explain the appearance of these immunoglobulins: either the thymocyte suspensions contain traces of red blood cells (J. M. Rolland, 1972, Pathology, 4(2): 85-122), or common surface antigens exist between T cells, B cells and erythrocytes, which at the current time is the most plausible hypothesis.

Techniques were then developed in order to improve the purity of the preparation. These techniques envisioned a step of hemadsorption, namely adsorption on human red blood cells.

This step of hemadsorption makes it possible to remove the majority of the undesirable antibodies, such as the anti-erythrocyte antibodies present in the initial immune serum. A step of removal of the anti-tissue antibodies, on human tissues (such as placenta), was also sometimes envisaged, in order to adsorb the anti-basal membrane antibodies in particular. Several anti-human thymocyte immunoglobulins prepared according to these techniques are now available on the market, such as Thymoglobuline® (Imtix-Sangstat), Tecelac® (Biotest), or else ATGF® (Fresenius) or ATGAM® (Upjohn).

However, the methods described which comprise a step of adsorption on human tissues or red blood cells still exhibit drawbacks. In particular, in carrying out these methods, a 30% decrease in the level of gammaglobulins contained in the serum, and therefore a not insignificant part of the antibodies of interest, is observed. In addition, the removal of the undesirable anti-erythrocyte antibodies is not complete. Now, these antibodies would be liable to cause the appearance of hemolytic anemia in treated patients. Finally, the use of human material, such as erythrocytes, even purified and made safe, in the method for isolating the anti-human thymocyte immunoglobulins, increases the potential risk of infection.

The authors of the present invention have therefore sought to develop an improved method for producing anti-human thymocyte immunoglobulins.

SUMMARY OF THE INVENTION

The present invention relates to a method with no step of adsorption on human biological material, for producing a preparation of anti-thymocyte immunoglobulins which is sufficiently pure for use in therapy in particular.

More precisely, a subject of the invention is a method for producing anti-purified human thymocyte immunoglobulins, which comprises the steps consisting in:
  (a) injecting a cellular preparation of human thymocytes into a specific-pathogen-free (SPF) animal;
  (b) collecting the immune serum produced by the animal;
  (c) isolating the anti-human thymocyte immunoglobulins from the serum, with no adsorption on human biological material.

More particularly, the expression "immunoglobulins from serum" is intended to mean the total fraction of gammaglobulins from the serum after immunization.

The expression "adsorption on human biological material" is intended to mean in particular hemadsorption on red blood cells or adsorption on human tissues (such as placenta in particular), stroma or crude extracts of these tissues.

DETAILED DESCRIPTION OF THE INVENTION

The SPF animals are breeding animals whose environment and food are strictly controlled according to health standards. Reference is also made to animals "with controlled health status". The SPF animals are bred in closed, sterilized compartments, the air environment being filtered, for example through a HEPA filter (sterilizing filtration), and the water and foodstuff being decontaminated before introduction, which makes it possible to eliminate any pathogenic element from their direct environment (Yanabe et al. Exp. Animal 48(2), 101-106 (1999)). The term "pathogen" here denotes an infectious agent capable of causing a clinical disease and/or of modifying the biological response of the animal with regard to the desired use. The SPF status refers to a list (which evolves) of microorganisms and of methods of control (clinical, serological, histological, or using culturing) for detecting the targeted microorganisms or, conversely, demonstrating their absence.

Use is preferentially made of horses or goats, more preferably rabbits, for the production of immune serum. In fact, only IgG1s are present in rabbit serum, which facilitates the process of antibody purification. Rabbit IgG also shows a high affinity for the human Fc receptor, allowing the development of powerful cytotoxic antibodies directed against human T cells.

The cellular preparation of human thymuses can be obtained either from cells of lines in culture, or from fresh thymocytes which are purified preferentially from human thymus fragments or optionally from, for example, suspensions of spleen, tonsils, lymph nodes, thoracic trachea or peripheral blood. The human thymus fragments can in particular be easily removed during surgical acts, in particular subsequent to cardiac surgery on children. Virological tests are carried out on the donor's blood in order to avoid any contamination and to eliminate any contaminated thymic fragment showing a positive serological result.

The injecting of the human thymocytes and the collecting of the immune serum from the SPF animal are carried out according to standard techniques of those skilled in the art.

Isolation of the anti-human thymocyte immunoglobulins from the serum makes it possible to eliminate the undesirable proteins. It can be carried out using, for example, ion exchange chromatography, preferably on a column, and/or one or more precipitations.

Advantageously, such a precipitation can be carried out in two successive steps using an immunoglobulin precipitating reagent. The reagent preferentially used is sodium sulfate.

The chromatography step enables retention of the loaded impurities by an ion exchange resin such as anions (DEAF). As regards the IgGs, they are not retained by the column and are rapidly removed from the column, which makes it possible to harvest them selectively. Chromatography on a specific affinity column, which removes the remaining undesirable antibodies, is also advantageous.

A subject of the invention is also the isolated antihuman thymocyte immunoglobulins which can be prepared using the method of the invention.

These immunoglobulins can also be designated "antihuman lymphocyte immunoglobulins" since they recognize human lymphocytes when they are brought into contact with these lymphocytes, for example when injected into patients for the purpose of immunodepletion.

Moreover, the present invention is also directed toward the use of these immunoglobulins for producing a medicinal product intended to decrease the quantity of circulating lymphocytes of the blood and of the lymphoid tissues in a human patient.

A subject of the invention is also a method of therapeutic treatment in which a therapeutically effective quantity of immunoglobulins thus obtained is administered to a patient requiring his or her quantity of lymphocytes to be decreased. These immunoglobulins are particularly useful in the context of organ transplants.

The anti-human thymocyte immunoglobulins prepared according to the method described above exhibit a greater specific activity than the anti-thymocyte immunoglobulins prepared using a method including a hemadsorption step, as emerges in Example 2.1 presented below.

Deleting the step of adsorption on human biological material makes it possible to produce immunoglobulins without any contact with a human derivative. This leads to the elimination of any possible viral contamination or contamination with unconventional agents of the prion type. In addition, any contamination associated with hemadsorption, namely contamination with the hemoglobin released by the human red blood cells during the hemolysis engendered by this step, is avoided.

The method of the invention makes it possible to obtain a preparation of anti-thymocyte immunoglobulins in which the number of immunoglobulins capable of cross reacting with other blood cells (erythrocytes, neutrophils, etc.) is considerably reduced. In addition, the fact that hemadsorption is not used in preparing the anti-thymocyte antibodies makes it possible not only to improve the safety aspect, but also reduces the length and the cost of the preparation method. In fact, hemadsorption conventionally uses whole human red blood cells which are fresh and formalin-treated, and requires large quantities of cells to be treated, making the production of antithymocyte immunoglobulins relatively restrictive in industrial terms.

The following examples illustrate the invention without limiting the scope thereof.

EXAMPLES

Example 1

Production of Immunoglobulins 1.1 Purification of Thymocytes

Human thymus fragments are, after removal and grinding, filtered and placed in suspension.

The cell suspension is then filtered through a nylon cloth and subjected to centrifugation at 1800 rpm at 5° C.

20 ml of Ficoll are added to 10 ml of cell solution containing 2 to $7 \times 10^9$ cells and the mixture is centrifuged at 2000 rpm at 5° C. Two subsequent centrifugations are carried out at 1800 rpm. The cellular preparations are then stored at 5° C. overnight and are then diluted before being injected into SPF rabbits. The thymocytes can also be conserved by freezing.

1.2 Isolation of Antibodies

The rabbit immune serum is collected in the course of several bleeds between D20 and D30, and can be frozen for storage. During the preparation, batches of serum are formed which are gradually returned to ambient temperature.

These batches of rabbit serum are decomplemented in order to remove the complement proteins, by bringing them to a temperature of 56□C±2□C for a period of 30 to 45 min.

The rabbit serum is purified for the immunglobulin fraction by chromatography on an anion exchange resin (DEAE) at ambient temperature followed by two precipitations with sodium sulfate.

After a further step of filtration, concentration and diafiltration, the anti-thymocyte immunoglobulins are pasteurized at a temperature of 60° C. for 10 hours in order to ensure the viral safety thereof.

According to one variant, the steps of filtration, concentration, diafiltration and precipitation of the immunoglobulin fraction (for example alcoholic fractionation of the COHN type or ammonium sulfate fractionation) can be carried out before the chromatography step.

The solution of immunoglobulins can, after formulation and sterilization by filtration, be conserved in the liquid state in a solution of 5 to 25 mg/ml or, according to one variant, in the lyophilized state. A series of quality controls is executed, including physicochemical tests, safety tests (presence of pyrogenic agents, of antiplatelet activity), sterility and purity tests and also lymphocytotoxic activity tests (inhibition of rosette formation in vitro and allogenic skin graft survival in monkeys).

Example 2

Comparative Analysis of the Effectiveness and the Innocuity of the Immunoglobulins Obtained Using the Method of the Invention, with Respect to Conventional Immunoglobulins (Obtained with Hemadsorption)

3.1 Measurement of the Specific Activity In Vitro

Two batches of immunoglobulins were used for the comparative study of the specific activity: a standard anti-thymocyte immunoglobulin (ATG) batch and a nonhemadsorbed ATG batch.

To determine the specific activity of the ATGs, i.e. to evaluate the quantity of immunoglobulins capable of binding to human lymphocytes, a technique of flow cytometry coupled to indirect immunofluorescence is used. Whole monkey blood (containing all blood cells) is incubated with the ATG batches at various concentrations. The excess of unattached immunoglobulins is rinsed off and a second antibody, labeled with fluorescein isothiocyanate (FITC), is added so as to attach to the bound ATGs. The amount of binding of the ATGs to the surface of the cells is then revealed after differentiation of the cells as a function of their size using flow cytometry.

The results show a greater specific activity of the non-hemadsorbed ATGs. Thus, to obtain the same binding to lymphocytes, 2.73 µg/ml of non-hemadsorbed ATG are necessary, where 7.23 µg/ml of standard ATG are necessary, i.e. 2.65 times more. The hemadsorption step therefore decreases the binding capacity and the specific activity of the ATGs.

3.2 Measurement of the Activity of the ATGs in Vivo in the Skin Graft Test in Monkeys Three groups of monkeys were selected for carrying out this test: a control group (n=5), a group receiving 5 mg/kg of standard ATG (n=8) and a group receiving 5 mg/kg of ATG not hemadsorbed (n=3) initially. A 50/50 dilution of the non-hemadsorbed ATGs is carried out in order to obtain a specific activity equivalent to that of the standard batch.

The skin graft test consists in performing, on D0, four allografts (originating from an animal in which at least two of the HLA antigenic determinants are different) and an autograft of skin on the back of each animal. The doses of ATG are then administered in vivo for three weeks from D-1.

The results show that the mean survival times of the allografts are equivalent for the two groups of treated monkeys: 23 days (±4.16) for the standard ATG group and 21.3 days (±7.3) for the non-hemadsorbed ATG group. They are also greater than the control: 9.4 days (±1.5).

The prolonging of the survival time of the skin graft correlates with the lymphocyte depletion induced by the administration of ATG. The lymphopenia follows an evolution which is comparable between the two batches: maximum decrease in the level of lymphocytes at D5, then gradual return to normal values around D20.

Consequently, the diluted batch of non-hemadsorbed ATGs is equivalent, in terms of effective in vivo in the primate, to the undiluted standard ATG batch.

3.3 Evaluation of the Risks of Hemolytic Anemia Subsequent to Administration of ATGs In the context of the same study, blood tests are carried out regularly until the end of the test and show that the evolution of the hemoglobin level is identical in the two groups of treated monkeys. A decrease in this level is observed up to D9, until this level gradually returns to normal values. Two phenomena are responsible for this evolution: firstly, the anemia is of the iatrogenic type, subsequent to the repeated taking of blood samples. This anemia is identical in the three groups of monkeys. Secondly, an effect specific to the ATGs causes a substantial decrease in the hemoglobin level from D1 in the treated groups, this decrease being identical with the standard ATG or with the non-hemadsorbed ATG.

In addition, in order to detect a possible hemolytic cause for the anemia, the levels of haptoglobin and of oromucoid are also measured. In the event of hemolysis, haptoglobin becomes unmeasurable. Now, these two levels increase from D4 for the two groups, this increase reflecting an inflammatory activity.

Thus, the hematologic safety evaluated in the animals treated with the non-hemadsorbed ATG is as satisfactory as in the animals treated with the hemadsorbed ATG.

The invention claimed is:

1. A method for producing a therapeutic preparation of anti-human thymocyte immunoglobulins for use in human therapy, comprising the steps of:
   a. injecting a cellular preparation of human thymocytes obtained from human thymus into a specific-pathogen-free (SPF) animal;
   b. collecting the immune serum produced by the animal; and
   c. isolating the anti-human thymocyte immunoglobulins from the collected immune serum;
   wherein said method includes no step of adsorption on human biological material in order to produce said therapeutic preparation of anti-human thymocyte immunoglobulins.

2. The method according to claim 1, wherein the SPF animal is a rabbit.

3. The method according to claim 1, wherein the isolation step (c) comprises a chromatography step.

4. The method according to claim 3, wherein the chromatography step comprises chromatography on an ion exchange resin on a column.

5. The method according to claim 4, wherein said ion exchange resin is an anion exchange resin.

6. The method according to claim 5, wherein said anion exchange resin is DEAE.

7. The method according to claim 3, wherein the chromatography step further comprises chromatography on a specific affinity column.

8. The method according to claim 3, wherein said isolation step (c) further comprises at least one precipitation step.

9. The method according to claim 8, wherein said at least one precipitation step uses an immunoglobulin-precipitating reagent.

10. The method according to claim 9, wherein said immunoglobulin-precipitating reagent is sodium sulfate.

11. The method according to claim 1, wherein the cellular preparation of human thymocytes obtained from human thymus used in step (a) comprises fresh human thymocytes.

* * * * *